US008562632B2

(12) United States Patent
Jakoubek

(10) Patent No.: US 8,562,632 B2
(45) Date of Patent: Oct. 22, 2013

(54) SHAFTED SURGICAL INSTRUMENT FOR REMOTE ACCESS SURGICAL PROCEDURES

(75) Inventor: Franz Jakoubek, Liptingen (DE)

(73) Assignee: Edwards Lifesciences Corporation, Irvine, CA (US)

( * ) Notice: Subject to any disclaimer, the term of this patent is extended or adjusted under 35 U.S.C. 154(b) by 127 days.

(21) Appl. No.: 12/885,331

(22) Filed: Sep. 17, 2010

(65) Prior Publication Data

US 2011/0071546 A1 Mar. 24, 2011

Related U.S. Application Data

(60) Provisional application No. 61/243,949, filed on Sep. 18, 2009.

(51) Int. Cl.
*A61B 17/04* (2006.01)

(52) U.S. Cl.
USPC ............................................. 606/148; 289/17

(58) Field of Classification Search
USPC ................. 606/138, 139, 144, 148, 205–211; 112/169; 289/17; 433/3, 4; D24/143, D24/152; 269/1, 2, 86–87.3; 81/300–312
See application file for complete search history.

(56) References Cited

U.S. PATENT DOCUMENTS

| | | | |
|---|---|---|---|
| 5,810,877 A | 9/1998 | Roth et al. | |
| 6,183,484 B1 * | 2/2001 | Matsutani et al. | 606/144 |
| 6,511,488 B1 * | 1/2003 | Marshall et al. | 606/148 |
| 2002/0049458 A1 | 4/2002 | Singhatat | |
| 2003/0220659 A1 * | 11/2003 | Schmieding et al. | 606/148 |
| 2004/0059350 A1 * | 3/2004 | Gordon et al. | 606/144 |
| 2004/0158125 A1 * | 8/2004 | Aznoian et al. | 600/106 |
| 2004/0254598 A1 | 12/2004 | Schumacher et al. | |
| 2006/0190016 A1 * | 8/2006 | Onuki et al. | 606/144 |
| 2007/0156172 A1 | 7/2007 | Alvarado | |
| 2007/0219566 A1 * | 9/2007 | Gambale | 606/142 |
| 2008/0097479 A1 | 4/2008 | Boehlke et al. | |

OTHER PUBLICATIONS

International Search Report, May 26, 2011.

* cited by examiner

*Primary Examiner* — Corrine M McDermott
*Assistant Examiner* — Robert Lynch
(74) *Attorney, Agent, or Firm* — AnneMarie Kaiser

(57) ABSTRACT

An instrument for use in minimally-invasive procedures generally including a pair of coaxially arranged shafts, an end-effector at the distal ends of the shafts, and an actuator at the proximal ends of the shafts. The end-effector is in the form of a suture holder which includes a first, fixed arm at a distal end of a first, fixed outer shaft, and a second, movable arm at a distal end of a second, movable inner shaft. The fixed arm includes a u-shaped end, which defines an opening adapted to receive a portion of an elongate flexible suture material. A closure pin fixed at an end of the movable arm moves back and forth, opening and closing the opening in the u-shaped end of the fixed arm. The closure pin extends from the movable arm into a pin guide opening through one leg of the u-shaped end of the fixed arm.

19 Claims, 3 Drawing Sheets

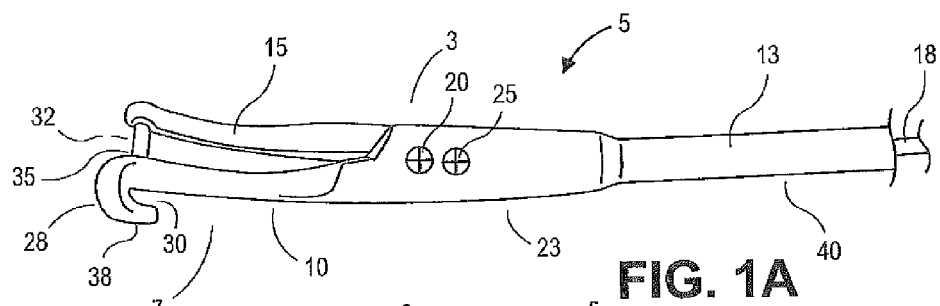
FIG. 1A
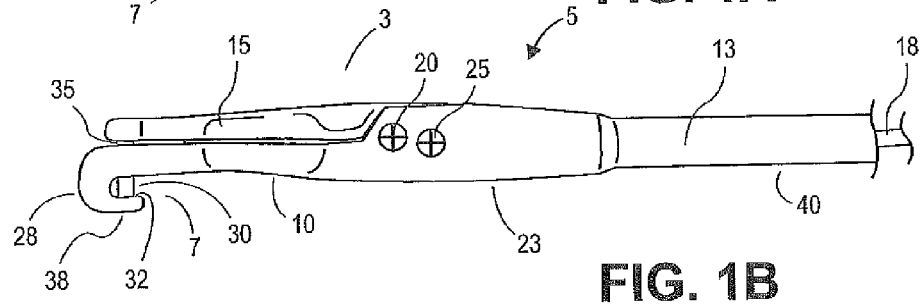
FIG. 1B
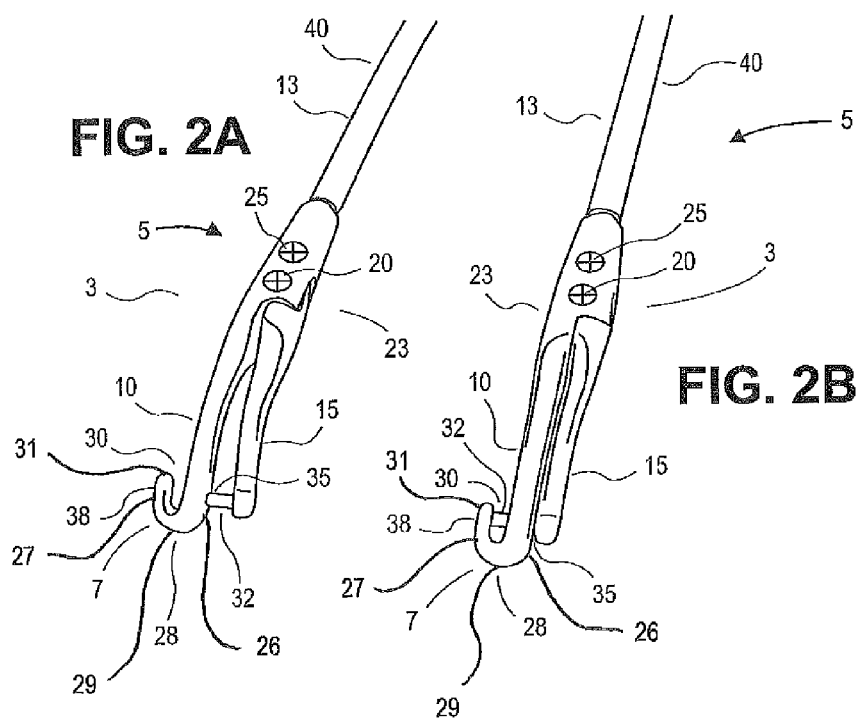
FIG. 2A
FIG. 2B

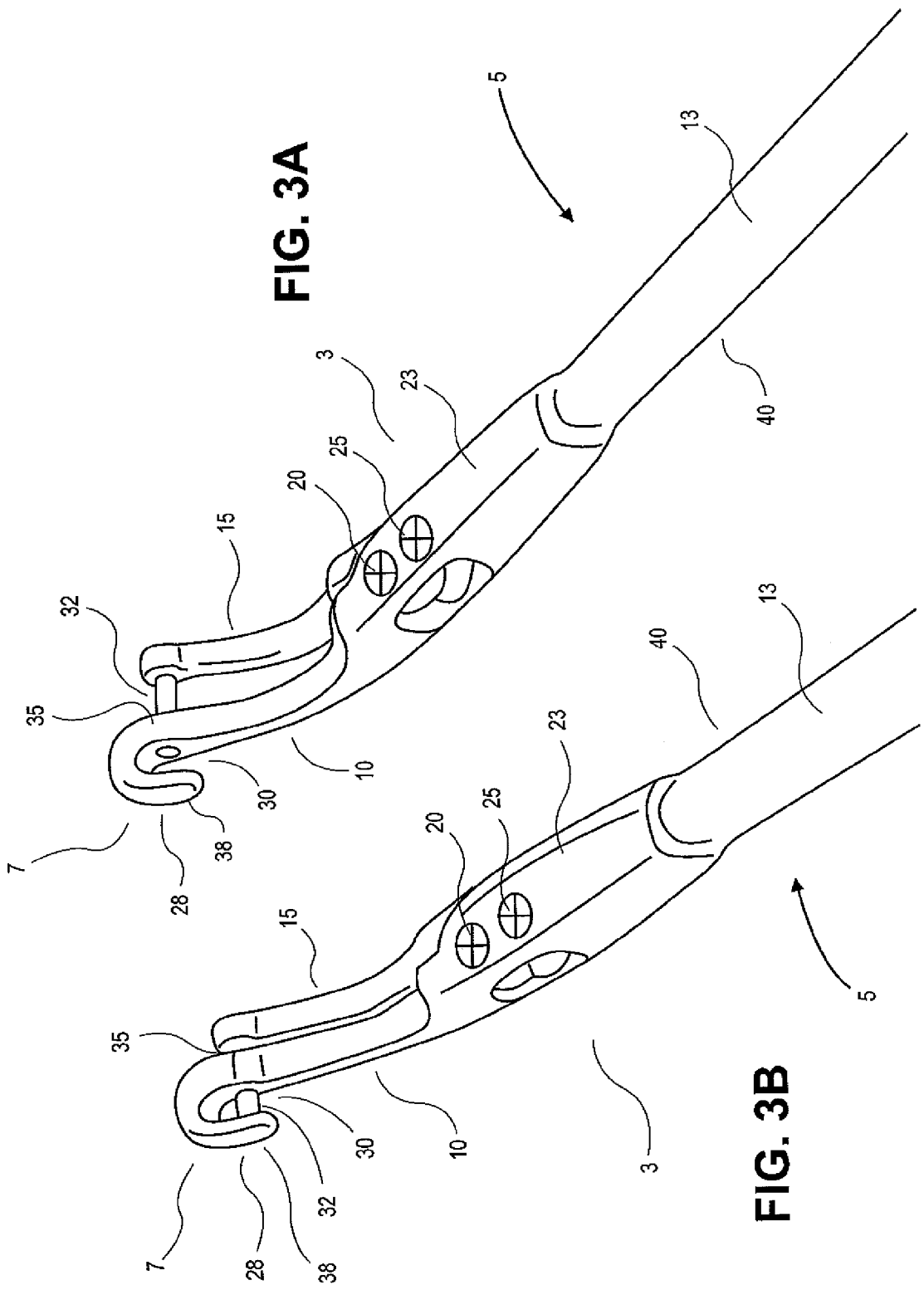

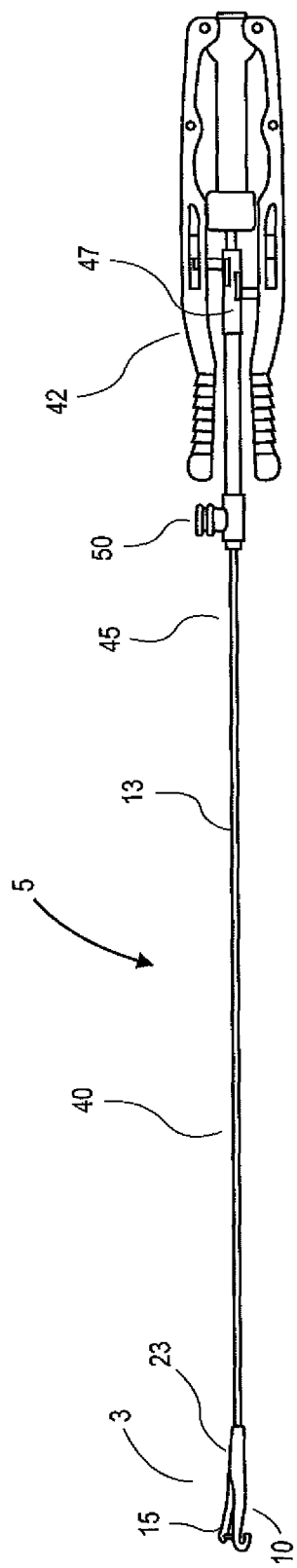
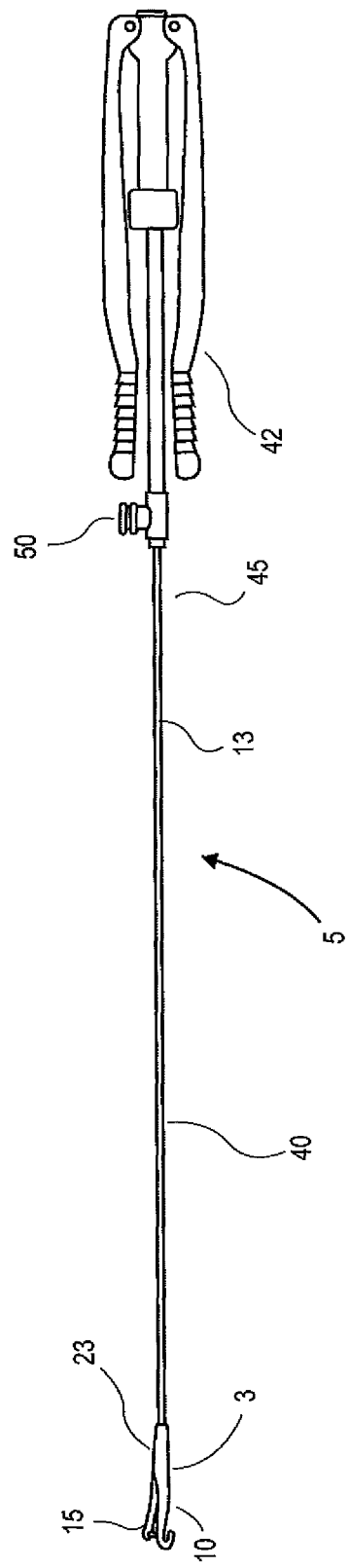
FIG. 4A
FIG. 4B

SHAFTED SURGICAL INSTRUMENT FOR REMOTE ACCESS SURGICAL PROCEDURES

CROSS-REFERENCE TO RELATED APPLICATIONS

This application claims priority from U.S. Provisional Patent Application No. 61/243,949, filed on Sep. 18, 2009 and entitled "Surgical Knot Pusher" which is hereby incorporated by reference in its entirety.

BACKGROUND OF THE INVENTION

Minimally invasive surgical techniques have emerged as an alternative to conventional surgical techniques to perform a plurality of surgical procedures. Minimally invasive procedures differ from conventional surgical procedures in that devices are introduced into the body through a small incision. As a result, trauma to the body is greatly reduced, thereby decreasing the recovery time of the patient.

One challenge presented when performing a minimally invasive technique is to remotely position and apply sutures to an area of interest. In conventional surgical techniques, the surgeon will approximate the tissue pieces by forcing a needle and suture material through various portions of the tissue to be approximated, and tying a knot in the suture material resulting in approximation. In contrast, in minimally invasive surgical techniques the surgeon's access to the approximation site is greatly reduced. Commonly, a surgical device will attach the suture material to the tissue. The surgeon will remotely form a knot in the suture material and advance the knot to the area of interest with a "knot pusher," thereby approximating the tissue.

Many surgical instruments include a working end or effector, such as a clamp, scissors, forceps, needle holder, graspers, pusher, etc. that is connected to a central shaft. Distal from the working end is typically a handle for grasping and manipulating the instrument. In many instances, the handle includes an actuating mechanism that is linked to and that actuates the working end or effector.

These devices permit an operator to push suture knots which have been formed extracorporeally towards tissue to be sutured. With respect to the aforementioned devices, it is desirable to have a system capable of intracorporeally positioning and applying a suture knot to an area of interest. Additionally, it is desirable to have a knot pushing system wherein the operator may cut and remove surplus suture material using the knot pushing device.

Many surgical instruments include a working end or effector, such as a knot pusher, suture holder, clamp, scissors, forceps, needle holder, graspers, etc. that is connected to a central shaft. Distal from the working end is typically a handle for grasping and manipulating the instrument. In many instances, the handle includes an actuating mechanism that is linked to and that actuates the working end or effector. At the distal end, the handle includes a linkage that can be manipulated by a user to actuate the end-effector.

SUMMARY OF THE INVENTION

The present invention provides an instrument for use in intricate, minimally-invasive procedures. The instrument generally includes a pair of coaxially arranged shafts, an end-effector at the distal ends of the shafts, and an actuator handle at the proximal ends of the shafts. The actuator includes a pair of generally straight arms pivotally coupled to a shaft. The links are coupled to a proximal portion of the arms for mechanical advantage.

The present invention provides a knot pushing device comprising an elongated shaft portion having a distal end, a proximal end, a fixed outer shaft, and a movable inner shaft coupled to the fixed outer shaft; the proximal end comprising an actuator handle; the distal end comprising a fixed arm at a distal end of the fixed outer shaft, and a movable arm at a distal end of the movable inner shaft; the fixed arm comprising at least one generally u-shaped end, which defines an opening adapted to receive a portion of an elongate flexible suture material, the u-shaped end having a pin guide opening, and a pin receiver opening; and wherein the movable arm comprises a closure pin. In other embodiments, the knot pushing device may contain a flush port.

The aforementioned features may be combined in a variety of different ways to form different embodiments. It should also be understood that the foregoing Summary is not a complete description of the inventive features and aspects of the invention. Other features and advantages of the present invention will become more apparent from the following Detailed Description, taken in conjunction with the drawings, and from the claims.

BRIEF DESCRIPTION OF THE DRAWINGS

FIG. 1a is a detailed view of the end-effector of an embodiment of the present invention in an open configuration;

FIG. 1b is a detailed view of the end-effector of an embodiment of the present invention in a closed configuration;

FIG. 2a is another detailed view of the end-effector of an embodiment of the present invention in an open configuration;

FIG. 2b is another detailed view of the end-effector of an embodiment of the present invention in a closed configuration;

FIG. 3a is another detailed view of the end-effector of an embodiment of the present invention in an open configuration;

FIG. 3b is another detailed view of the end-effector of an embodiment of the present invention in a closed configuration;

FIG. 4a illustrates the end-effector, shaft and handle portions of an embodiment of the present invention; and FIG. 4b illustrates another embodiment of the end-effector, shaft and handle portions of the present invention.

REFERENCE NUMBERS

The following table summarizes the reference numbers used in conjunction with the accompanying Figures:

| | |
|---|---|
| 3 | end-effector |
| 5 | knot pusher |
| 7 | suture holder |
| 10 | fixed arm |
| 13 | fixed outer shaft |
| 15 | movable arm |
| 18 | movable inner shaft |
| 20 | pivot center |
| 23 | flared portion |
| 25 | link junction |
| 26 | first leg |
| 27 | second leg |
| 28 | u-shaped end |
| 29 | connecting portion |
| 30 | opening |

-continued

| 31 | free end |
| --- | --- |
| 32 | closure pin |
| 35 | pin guide opening |
| 38 | pin receiver opening |
| 40 | elongate shaft portion |
| 42 | movable actuator handle |
| 45 | proximal end |
| 47 | latching mechanism |
| 50 | flush port |

DETAILED DESCRIPTION OF A PREFERRED EMBODIMENT

The following description of embodiments refers to the accompanying drawings, which illustrate specific embodiments of the invention. Other embodiments having different structures and operation do not depart from the scope of the present invention. These embodiments merely illustrate the concepts of the invention as applied to specific surgical instruments.

The knot pushing device of the present invention is generally used in minimally invasive surgical procedures, which typically utilize relatively small incisions, to precisely apply and position a knot. The device and method disclosed herein are of particular value when a surgeon or other clinician is unable to tie a suture knot directly at the surgical site.

As those skilled in the art will appreciate, the present invention may be utilized as a handheld device or, in the alternative, as a catheter delivered implement. It is anticipated as being within the scope of the present invention to produce a knot pusher capable of functionally delivering knots formed with a plurality of suture sizes to various locations within a body.

The instrument generally includes a pair of coaxially arranged shafts, an end-effector at the distal ends of the shafts, and an actuator at the proximal ends of the shafts. The actuator includes a pair of generally straight arms pivotally coupled to a shaft. The links are coupled to a proximal portion of the arms for mechanical advantage. The end-effector comprises a surgical knot pusher in the form of a closable suture holder.

FIGS. 1a and 1b illustrate an end effector 3 for a surgical knot pusher 5 that embodies features of this invention. This end effector is in the form of a closable suture holder 7. FIG. 1a shows the suture holder in an open configuration; FIG. 1b shows the suture holder in a closed configuration.

The suture holder 7 includes a first, fixed arm 10 at a distal end of a first, fixed outer shaft 13, and a second, movable arm 15 at a distal end of a second, movable inner shaft 18. The cylindrical inner shaft can slide back and forth inside the tubular outer shaft.

The movable arm 15 pivots around a pivot center 20 inside a flared portion 23 between the outer shaft 13 and the fixed arm 10. An end of the movable arm 15 is linked to the distal end of the inner shaft 18 at a link junction 25 inside the flared portion. The movable arm is configured so that movement of the inner shaft inside the outer shaft pivots the movable arm about the pivot center in relation to the fixed position of the fixed arm.

The fixed arm includes a u-shaped end 28 formed from a first leg 26, a second leg 27, and a connecting portion 29, which defines proximally-facing opening 30 adapted to receive a portion of an elongate flexible suture material (not shown). The second leg terminates in free end 31. A closure pin 32 fixed at an end of the movable arm 15 moves back and forth, opening and closing the opening in the u-shaped end 28 of the fixed arm 10. The closure pin extends from the movable arm into a pin guide opening 35 through one leg of the u-shaped end of the fixed arm. Note that the fixed arm and movable arm may be curved along the lengths thereof.

Pulling the inner shaft 18 in a direction toward a proximal end of the instrument 5 pivots the movable arm 15 towards the fixed arm 10, which moves the closure pin 32 further through the pin guide 35, across the opening 30 in the u-shaped end 28 of the fixed arm 10, and into a pin receiver opening 38 on a leg of the u-shaped end opposite the leg in which the pin guide 35 is formed. The closure pin is thereby moved to close the suture material receiving opening 30 in the fixed arm's u-shaped end 28. A portion of the elongate flexible suture material can thereby be retained securely inside the u-shaped opening in the fixed arm, so that the suture material can be manipulated securely as desired by a user of the device, without any substantial danger of the suture material slipping out of the (closed) u-shaped opening at the distal end of the device.

FIGS. 2a and 2b show the knot pusher's end effector 3 and its constituent elements from a different point of view. In FIG. 2a the u-shaped suture receiving opening 30 is open. In FIG. 2b the u-shaped opening is closed, with the closure pin 32 on the movable arm 15 extending through the pin guide opening 35 and into the pin receiver opening 38, these two openings being located on opposite legs of the u-shaped end 28 of the fixed arm 10.

FIGS. 3a and 3b show the end effector 3 from still another angle. In FIG. 3a the opening 30 is open; in FIG. 3b the opening is closed.

Two knot pusher surgical instruments 5 that embody the invention are shown in FIGS. 4a and 4b. Each of these instruments includes an end effector 3 as described above. Each of the end effectors is located at a distal end of an elongate shaft portion 40 of the instrument. Each of the instruments includes a movable actuator handle 42 at a proximal end 45 of the shaft portion.

The actuator handles 42 may be generally of a type described, e.g., in U.S. Pat. No. 5,810,877, the disclosure of which is hereby incorporated fully by reference into this disclosure. The actuator handle on the device in FIG. 4a includes a latching mechanism 47 with which a user of the device can lock the actuator handle so that the end effector 3 is held in its closed configuration until the latch is released. The actuator handle on the device in FIG. 4b includes no such latching mechanism.

Each of the devices 5 in FIGS. 4a and 4b includes a flush port 50 through which a fluid can be injected down the length of the outer shaft 13 and out through the end effector 3, e.g., for clearing a surgical field around the end effector to allow better visualization during a surgical procedure, or for cleaning the end effector after the device has been used.

Those skilled in the art will appreciate that the device 5 may be manufactured from a plurality of materials, including, for example, polycarbonate or polyacetate, thereby providing a relatively rigid device. In an alternative embodiment of the present invention, the device 5 may be manufactured from moderately flexible materials such as, for example, polyvinyl chloride or braided cable, thereby enabling catheter-based applications. Alternatively, the device 5 of the present invention may contain at least one internal lumen.

Those skilled in the art of minimally invasive surgery will appreciate that the end effector 3 may comprise additional devices. For example, a visualization device may be disposed on the end effector 3, thereby enabling the operator to visualize the suture placement. The visualization device may be passive in the form of a radio-opaque or echo-genic material for visualization by x-ray or ultrasound. In an alternate embodiment, the visualization may be achieved with an ultrasonic or fiber optic probe coupled to the device. In an alternative embodiment end effector 3 may further comprise a medicament applicator in communication with at least one medicament lumen located within the fixed outer shaft 13, thereby enabling the delivery and application of a medicament to the tissue containing or surrounding the suture.

While particular forms of the invention have been illustrated and described, it will be apparent that various modifications can be made without departing from the spirit and scope of the invention. Accordingly, it is not intended that the invention be limited, except as by the appended claims.

What is claimed is:

1. A knot pushing device comprising:
    an elongated shaft portion having a distal end, a proximal end, a fixed outer shaft, and a movable inner shaft coupled to the fixed outer shaft;
    the proximal end comprising an actuator handle;
    the distal end comprising a fixed arm at a distal end of the fixed outer shaft, a generally u-shaped end extending from a distal end of the fixed arm, and a movable arm at a distal end of the movable inner shaft, wherein the movable arm is positioned on a first side of the fixed arm;
    the generally u-shaped end comprising a first leg, a connecting portion, and a second leg, wherein the first leg extends distally from the fixed arm, wherein the connecting portion extends radially away from the fixed arm in a direction away from the movable arm, and wherein the second leg extends proximally away from the connecting portion, wherein the second leg comprises a free end, wherein the generally u-shaped end defines a proximally-facing opening adapted to receive a portion of an elongate flexible suture material, the first leg of the u-shaped end comprises a pin guide opening, and wherein the second leg of the u-shaped end comprises a pin receiver opening;
    wherein the actuator handle is configured to move the movable arm with respect to the fixed arm and thereby move the knot pushing device from an open configuration to a closed configuration; and
    wherein the movable arm comprises a closure pin, wherein the closure pin extends at least partially through the pin guide opening but not into the pin receiver opening when the knot pushing device is in the open configuration, and wherein the closure pin extends through the pin guide opening and across the opening of the u-shaped portion and into the pin receiver opening when the knot pushing device is in the closed configuration.

2. The device of claim 1 wherein the proximal end further comprises a flush port.

3. The device of claim 1 wherein the proximal end further comprises a latching mechanism.

4. The device of claim 1 wherein the elongated shaft portion is rigid.

5. The device of claim 1 wherein the elongated shaft portion is flexible.

6. The device of claim 1 wherein the elongated shaft portion is a catheter.

7. The device of claim 1 wherein the elongated shaft portion contains at least one lumen therein.

8. The device of claim 1 wherein the fixed arm further comprises a flared portion.

9. The device of claim 1, wherein the fixed arm and movable arm are curved along the lengths thereof.

10. A knot pushing device, comprising:
    an elongated shaft portion comprising:
    a shaft distal end;
    a shaft proximal end;
    a first arm and a second arm extending distally from the shaft distal end, wherein the first arm and second arm are movable with respect to each other to define an open configuration wherein a distal end of the first arm is spaced a first distance away from a distal end of the second arm, and to define a closed configuration wherein the distal end of the first arm is spaced a second distance away from the distal end of the second arm, wherein the first distance is greater than the second distance;
    an actuator handle positioned at the shaft proximal end, wherein the actuator handle is configured to effectuate relative movement between the first arm and the second arm to effectuate a transition between the open configuration and the closed configuration;
    wherein the first arm comprises a generally u-shaped end, wherein the generally u-shaped end comprises a proximally-facing suture opening, a pin guide opening, and a pin receiver opening, wherein the pin guide opening and pin receiver opening are positioned on opposite sides of the proximally-facing suture opening;
    wherein the second arm comprises a closure pin extending sideways therefrom in a direction toward the first arm, wherein the closure pin extends at least partially into the pin guide opening without extending across the proximally-facing suture opening when the first and second marts define the open configuration, and wherein the closure pin extends through the pin guide opening and across the proximally-facing suture opening and into the pin receiver opening when the first and second arms define the closed configuration.

11. The device of claim 10 wherein the proximal end further comprises a flush port.

12. The device of claim 10 wherein the proximal end further comprises a latching mechanism.

13. The device of claim 10 wherein the elongated shaft portion is rigid.

14. The device of claim 10 wherein the elongated shaft portion is flexible.

15. The device of claim 10 wherein the elongated shaft portion is catheter.

16. The device of claim 10 wherein the elongated shaft portion contains at least one lumen therein.

17. The device of claim 10 wherein the fixed arm further comprises a flared portion.

18. The device of claim 10, wherein the fixed arm and movable arm are curved along the lengths thereof.

19. The device of claim 18, wherein the fixed arm and movable are having matching curves along the lengths thereof.

* * * * *